United States Patent [19]
Höök et al.

[11] Patent Number: 5,980,908
[45] Date of Patent: *Nov. 9, 1999

[54] BACTERIAL CELL SURFACE PROTEIN WITH FIBRONECTIN, FIBRINOGEN, COLLAGEN AND LAMININ BINDING ABILITY, PROCESS FOR THE MANUFACTURE OF THE PROTEIN AND PROPHYLACTIC TREATMENT

[75] Inventors: Magnus Höök, Birmingham, Ala.; Kjell Martin Lindberg, Uppsala; Torkel Mikael Wadström, Knivsta, both of Sweden

[73] Assignee: Alfa Laval AB, Tumba, Sweden

[*] Notice: This patent is subject to a terminal disclaimer.

[21] Appl. No.: 08/118,697

[22] Filed: Sep. 10, 1993

Related U.S. Application Data

[62] Continuation of application No. 07/977,151, Nov. 16, 1992, abandoned, which is a division of application No. 07/801,593, Dec. 5, 1991, Pat. No. 5,189,015, which is a continuation of application No. 06/840,580, filed as application No. PCT/SE85/00227, May 30, 1985.

[51] Int. Cl.$^6$ ................................................. A61K 39/085
[52] U.S. Cl. ........................... 424/243.1; 424/823; 514/2; 530/350
[58] Field of Search .................................... 424/92, 243.1, 424/823; 422/88; 530/350; 514/2

[56] References Cited

U.S. PATENT DOCUMENTS

| | | |
|---|---|---|
| 3,917,818 | 11/1975 | Botes . |
| 4,197,290 | 4/1980 | Yoshida . |
| 4,312,942 | 1/1982 | Blobel et al. . |
| 4,327,082 | 4/1982 | Armitage . |
| 4,425,330 | 1/1984 | Norcross et al. . |
| 4,444,343 | 4/1984 | Buchannan et al. . |
| 4,645,757 | 2/1987 | Hjerten et al. . |
| 4,784,989 | 11/1988 | Hook et al. . |
| 4,795,803 | 1/1989 | Lindberg et al. . |
| 5,320,951 | 6/1994 | Hook et al. . |

FOREIGN PATENT DOCUMENTS

| | | |
|---|---|---|
| 0163623 | 12/1985 | European Pat. Off. . |
| 0294349 | 12/1988 | European Pat. Off. . |
| 0342173 | 11/1989 | European Pat. Off. . |
| 0343137 | 11/1989 | European Pat. Off. . |
| 0397633 | 11/1990 | European Pat. Off. . |
| WO-85/05037 | 11/1985 | WIPO . |
| WO 92/02555 | 2/1992 | WIPO . |

OTHER PUBLICATIONS

Abrahmsen et al.—*Nucl. Acid Res.* 14(18):7487–7500 (1986).
Chhatwal et al.—*Comp. Immunol. Microbiol. Infect. Dis.* 10(2):99–108 Abstract (1987).
Duggleby et al.—*Nuc. Acid. Res.* 11(10):3065–3076 (1983).
Espersen et al.—*Infect. and Immun.* 37(2):526–531 (Aug. 1982).
Flock et al.—*EMBO J.* 6(8):2351–2357 (1987).
Froman et al.—*J. Biol. Chem.* 262(14):6564–6571 (1987).
Keil–Dlouha et al.—*Biochem. Biophys. Acta.* 727:115–21 (1983).
Lofdahl et al.—*Proc. Natl. Acad. Sci.* 80:697–701 (Feb. 1983).
Mamo et al.—*Micro. Pathog.* 2(6):417–424 Abstract (1987).
McGavin et al.—*J. Biol. Chem.* 266(13):8343–7 (1991).
Myhre—*J. Med. Microbiol.* 18(2):189–196 Abstract (1984).
Myhre et al.—*Infect. Immun.* 40(1):29–34 (1983).
Nuesch et al.—*Gene* 32:243–249 (1984).
Overbeeke et al.—*J. Mol. Biol.* 163:513–532 (1983).
Raja et al.—*Infect. Immun.* 58(8):2593–8 (1990).
Ryden et al.—*J. Biol. Chem.* 258(5):3396–3401 (Mar. 1983).
Sambrook et al.—*Molecular Cloning: A Laboratory Manual,* (2d), 6.39–6.43, B.9 (1989).
Signas et al.—*Proc. Natl. Acad. Sci.* 86:699–703 (1989).
Switalski et al.—*Eur. J. Clin. Microbiol.* 1:381–387 (1982).
Beachey et al. J. of Infect. Dis 143(3):325–345. 1981.
Funderberg et al. (Ed) "Basic and Clinical Immunology" Published by Lange Medical Publications (CA) 1980 see p. 606.
R.M. Chanock et al. (ed.), "Vaccines 95, Molecular Approaches to the Control of Infectious Diseases", published by Cold Spring Harbor Laboratory Press, see pp. 249–255, 1995.

*Primary Examiner*—Patricia A. Duffy
*Attorney, Agent, or Firm*—Burns, Doane, Swecker & Mathis, L.L.P.

[57] ABSTRACT

The invention is concerned with a vaccine composition comprising an effective amount of an isolated protein derived from *Staphylococcal aureus* having the ability to bind fibronectin. The protein has a molecular weight of 165,000 daltons and optionally also contains a protein having a molecular weight of 87,000 daltons. The protein has the ability to elicit antibody production and a level of protein to elicit antibody production. The level of protein is sufficient to produce protection upon challenge with a *Staphylococcus aureus* bacterial strain in a mammal, particularly a ruminant, by forming antibodies against the *Staphylococcus aureus* bacterial strain.

8 Claims, No Drawings

BACTERIAL CELL SURFACE PROTEIN WITH FIBRONECTIN, FIBRINOGEN, COLLAGEN AND LAMININ BINDING ABILITY, PROCESS FOR THE MANUFACTURE OF THE PROTEIN AND PROPHYLACTIC TREATMENT

This application is a continuation of application Ser. No. 07/977,151, filed Nov. 16, 1992, now abandoned; which is a divisional application of application Ser. No. 07/801,593, filed Dec. 5, 1991, now U.S. Pat. No. 5,189,015; which is a continuation application of application Ser. No. 06/840,580, filed Jan. 21, 1986, now abandoned, which is a 371 of PCT/SE85/00227 filed May 30, 1985.

DESCRIPTION

1. Technical Field

The present invention relates to a cell surface protein having an ability of binding to fibronectin, fibrinogen, collagen, and/or laminin, process for its preparation, as well as the use of such a cell surface protein.

The object of the present invention is to obtain a possibility of blocking fibronectin, fibrinogen, collagen, and/or laminin in a traumatic wound tissue in order to prevent adherence of pathogenic bacterial strains on fibronectin, fibrinogen, collagen, and/or laminin.

2. Background of the Invention

*Staphylococci* and *streptococci* are usually often regarded as a group of gram positive bacteria, which develops purulent matter (pus) at infections, so called pathogenic cocci. This group does not only contain the classical *Staphylococcus aureus* and *Streptococcus pyogenes* (group A *streptococcus*), but also other *staphylococci* and *streptococci*, such as *Stachylococcus epidermis, Staphylococcus haemolyticus, Staphylococcus hyicus, streptococci* of Groups B, C, G, and H, *Viridans streptococci*, etc. Even gram negative bacteria such as *Escherichia coli* can cause such infections.

These pathogenic bacterial strains causes different infections in man and in animals all the way from small self-healing skin infections, to serious sepsis (blood infection). At the infection of animals by these strains the animals are not only suffering, but also great economical damages are caused to the others of the animals due to production cut-off. Niastitis in milking cows is such an economically damaging infection.

In man such bacterial strains cause i.a. heart valve infections, but also other infections as the commonly known "hospital illness", i.e., most often an infection of an open wound, which shows difficulties in healing, can produce large amounts of pus, and can cause reoperation. Particulary, the heart valve infections threatens risk groups already exposed within the hospital care.

The term wound used means that normally covering epithet cellular layer, and other surface structures have been damaged by mechanical, chemical, or other influence. The term wound can hereby be divided into two main groups, viz: surface wounds, and deep wounds. The term surface wound means a trauma on the surface of the body or a surface in direct connection to the cavities of the body, i.e., the gastro-intestinal duct, mouth cavity, urethra, milk ducts, etc. The term deep wounds means trauma in the inner of a body caused by violent outer assault or by surgical Incisions in different tissues.

When a wound is caused, fibronectin, fibrinogen, collagen, and/or laminin are exposed in the wound tissue. These proteins form together with so called proteoglucans a net work structure in different reinforcement tissues, and is the structure onto which connective tissue (fibroblasts) and epithet cells grow at a natural wound healing.

The natural wound healing can, however, be prevented by pathogenic bacteria colonizing therein, primarily by pyogenic cocci, and secondly by other pathogenic strains, such as *E. coli* and other gram negative rod shaped bacteria.

Examples of such a colonizing of a tissue damage are:
i) colonizing of wounds in skin and connective tissue, which wounds have been caused by a mechanical violence, chemical damage, and/or thermical damage;
ii) colonizing of wounds on mucuous membranes, such as in the mouth cavity, or in the mammalian glands, urethra, or vagina;
iii) colonizing on connective tissue proteins, which have been exposed by a minimal tissue damage (microlesion) in connection with epithet and endothel (mastitis, heart valve infection).

DESCRIPTION OF THE PRESENT INVENTION

It has now surprisingly been shown possible to isolate proteins from bacterial cell surfaces, which proteins adhere to fibronectin, fibrinogen, collagen and/or laminin, which cell surface proteins are derived from bacterial strains mentioned above.

Such cell surface proteins can thereby be used for the treatment of wounds, e.g., for blocking protein receptors or for immunization (vaccination). In the latter case the body creates specific antibodies, which can protect against invasion of bacterial strains comprising such a cell surface protein. Hereby the antibodies block the adherence of the bacterial strains to a damaged tissue.

The characteristics of the present invention are evident from the accompanying claims.

By means of the present invention it is thus achieved that pathogenic bacterial strains can be effectively prevented from colonizing a traumatic wound tissue.

When using the present cell surface proteins for the purpose of immunization (vaccination) in mammals including man, the protein is dispersed in a sterile, isotonic saline solution, optionally while adding a pharmaceutically acceptable dispersing agent.

A suitable dosage to obtain immunization is 0.5 to 4 $\mu$g of cell surface proteins per kg bodyweight and injection of immunization. In order to obtain a durable immunization, vaccination should be carried out at three consecutive occasions with an interval of 1 to 3 weeks. Furthermore, one carries out the immunization in accordance with science and tested practise.

When using the present cell surface proteins for topical, local application the protein is dispersed in an isotcnic saline solution to a concentration of 25 to 200 $\mu$g per ml. The wounds are then treated with such an amount only to obtain a complete wetting of the wound surface. For an average wound thus only a couple of millilitres of solution are used in this way. After treatment using the protein solution the wounds are suitably washed with isotonic saline solution or another suitable wound treatment solution.

Below, an immunization of young cows against mastitis is shown. Topical use of cell surface protein can also be used for preventing mastitis by treating udders/teats with a solution comprising cell surface proteins, which prevents pathogenic, mastitis-inducing organisms to adhere thereto.

In accordance with the invention a mixture of cell surface proteins with different binding properties can be used, particularly if the binding properties of an infecting, bacterial strain are unknown, and there is a great demand for a rapid prevention of a massive bacterial epidemic infection; or the infection is caused by a mixture of bacteria.

The invention will be described more in detail in the following with reference to some Examples.

EXAMPLE

A strain of Staphylococcus aureus, which binds to fibronectin was grown on a liquid medium (TS-broth), trypticase-soya-extract (Oxoid, Ltd., England).

After finished growth the bacteria were isolated by centrifugation and were flashed with a saline solution (0.9% NaCl in water). The bacteria were then decomposed using a bacteriolytic enzyme (Lysostaphin$^R$, Sigma, 5 mg/litre of cell culture). Fibronectin binding components were isolated by affinity chromatography on immobilized fibronectin bound to a dextrane gel (Sepharose, CL-4B, cyanobromide activated). The fibrorectin binding componerts were then eluated by adding chaotropic ions (e.g. NaSCN, KSCN) in an aqueous solution. The eluation can also be carried out using an acidic solution, acetic acid solution having pH<3.

Fibronectin binding components consisting of proteins having their molecular weights within the range of 11,000 to 165,000, preferably 40,000 to 165,000 were isolated. The proteins may comprise a carbohydrate residue, whereby, however, it is the protein residue which is fibronectin binding, which is shown by the fact that the effect is totally eliminated after a treatment using protease, or heating to 80 to 100° C.

The amino acid composition of the protein components obtained is evident from the Table below:

TABLE

| Amino Acid | Residues per 1000 amino acids | |
|---|---|---|
| | $M_w$ = 155K/ | $M_w$ = 87K |
| Aspartic acid | 146 | 134 |
| threoine | 107 | 103 |
| Serine | 65 | 78 |
| Glutamine | 171 | 151 |
| Proline | 62 | 58 |
| Glycine | 79 | 84 |
| Alanine | 46 | 47 |
| Cysteine[a] | 2.3 | n.d |
| Valine | 78 | 86 |
| Methionine[a] | 5.8 | n.d. |
| Isoleucine | 47 | 38 |
| Leucine | 40 | 46 |
| Tyrosine | 23 | 41 |
| Phenylalanine | 20 | 36 |
| Tryptophane[b] | 24 | 31 |
| Histidine | 32 | 30 |
| Lysine | 63 | 66 |
| Arginine | 12 | — |

[a] Amino acid determined after a performic acid oxidation of a sample
[b] Amino acid calculated from an absorbance at 280 nm and tyrosine content.
n.d. = not determined In the Example the affinity chromatography has been used for purification/isolation of the protein. Other biochemical separaticni methods are ion exchange chromatography, and molecular sieve; electrophoresis incl. isotacophoresis; electrofocusing.

A conventional cultivation of S. aureus gives a cell surface protein of the above. For an efficient industrial production of receptors for vaccine, and other care the gene needs to be cloned In a suitable organism in order to obtain high yields.

A purified fibronectin binding cell surface protein has proven to be immunogenous at the immunization of rabbit and ruminants, and has thereby developed formation of antibodies.

Test 1.

Vaccination of SRB-heifers (1:st calf cow) with a fibronectin binding protein in accordance with the Example above.

Three SRB-heifers (Swedish Red-and-White Cattle) were vaccinated subcutaneously in the thorax region using 400 $\mu$m of fibronectin binding component ($M_w$ 165,000 and 87,000). These injections were repeated twice with 14 days in between. Antibody determinations in serum and in milk by means of ELISA-method (Enzyme Linked Immuno Sorbent Assay) showed a very potent immune response determinable in large dilutions of milk and serum already at the moment for the second immunization.

Two weeks after the second injection, i.e., at the moment for the third immunization injection the immuno response was regarded as enough stimulated to carry out an experimental udder infection (mastitis) in the three animals. These three animals, as well as two control animals from the same stock vere exposed to an experimental udder infection using a strongly udder pathogenic strain isolated from acute bovine mastitis (S. aureus) in order to develop mastitis in the five animals. The test was carried out by washing, dispersing in an isotonic saline solution and then infecting into the teat and udder cavity using a standardized injection technique, 500 bacteria from a bacterial cultivation grown in a broth medium (TS-broth).

The following results were obtained:

i) very sparse growth in certain milk samples from vaccinated cows, only;

ii) very high number of bacteria in most milk samples from non-vaccinated animals;

iii) cell count determinations showed generally low cell counts in the vaccinated animals;

iv) cell count determinations showed gererally high cell counts in the non-vaccinated animals:

v) the vaccinated animals produced unchanged volumes of milk;

vi) the non-vaccinated animals showed markedly decreased milking volumes (>10%);

vii) determination of acute phase reactants type "C reactive protein", and albumine in the vaccinated animals showed no change of the values obtained prior to the innoculation;

viii) determination of acute phase reactants type "C reactive protein", and albumine in the non-vaccinated animals showed strongly increased values.

The results obtained show that antibodies against fibronectin binding protein are secreted into udder and are present in local wound lesions in an amount enough to sterically preventing the surface receptors of an infecting bacterial strain to bind to exposed fibronectin in the udder tissue.

Test 2.

Blocking of an infection in an open skin wound by wound treatment using fibronectin binding cell surface protein from S. aureus.

Stardardized wound damages (2×2 cm) were made on the back of pigs (20–25 kgs) using a so called dermatom. These wounds placed in two rows of 8 wounds on each side of the spine were subjected to a thermical damage (250° C., 3 min). After thermical treatment the wounds were covered with a sterile bandage for 1.5 hrs, whereupon the wounds were infected with *S. aureus* strain (SA 113(83A)). Prior to bacterial infection the wounds on one side of the spine were treated with fibronectin binding cell surface protein, according to the Example above, solved in a sterile isotonic saline solution (100 μg per ml of NaCl-solution). In wounds pretreated in this way the development of an infection was prevented by, at the same time, washing the wounds twice a day using a sterile isotonic saline solution. Non-treated wounds showed in the lesions, bad infections within 2 to 4 days although washing twice a day using NaCl-solution; infections which did not heal untreated with antibiotics during an observation period of one week.

The results of this experiment show that surface exposed fibronectin is blocked by pretreating lesions using 100 μg/ml in NaCl, in such a way that infections are preverted. Bacteria applied can easily be removed by rinsing which is impossible in wounds not treated with cell surface protein.

Besides fibronectin other connective tissue binding proteins have been detected in different microorganisms, which bind to those connective tissue structures present in men and animal, viz. collagen, and laminin according to the table below:

|  | Fibrnectin | Collagen | Laminin |
| --- | --- | --- | --- |
| Staphylococci (different types) | + | + | –[1] |
| Streptoccocci (Group A, C, G, H, opt. B) | + | + | + |
| *Escherichia coli* | + | –[1] | + |

[1] not yet tested
+denotes presence

Test 3.

The binding of *Staphylococci* to immobilized fibronectin—a model to simulate binding to traumatic tissue (surgical wounds and mastitis).

A polymer surface was treated with different serum proteins, such as albumine and fibronectin. The polymer surface was then incubated with the respective protein dispersed in a sodium phosphate buffered saline solution (0.2 M sodium phosphate, pH 7.4, and 0.145 M NaCl) for 2 hrs at ambient temperature. The polymer surface was then dried by blowing air using a fan. Then the treated surface was subjected to a *Staphylococci* (strain SA 113(83A)) in a buffer solution, and dispersed in the oresence of bovine milk, respectively. Already after a couple of minutes an uptake of bacteria was determined in both these testing systems, while a surface treated in the same way using albumine in the same, and in a 10-fold higher concentration of protein solution does not show an active bacterial uptake (untreated surface is however hydrophobic and binds *staphylococci* unspecific). The binding of strain SA 113(83A) can be inhibited by first incubating the bacteria with an antiserum obtained from rabbit vaccinated with a purified receptor protein.

Test 4.

In a similar way a surface has been treated with laminin, and then, as above, bacteria have been added, in this case a Group A *streptococcus* strain. Thereby it has been shown that the *strepococcus* strain binds to the surface.

Test 5.

A polymer surface was treated with fibronectin (immobilized) in accordance with Test 3 above. Then the surface was treated with a cell surface protein ($M_w$ 87,000) of Example 1 above solved in a physiologic Saline solution, 100 μg per ml. Then the surface was treated with a *Staphylococci* (strain SA 113(83A)) dispersed in a buffer solution (phosphate buffer, 0.2 M Na-phosphate, pH 7.4, and 0.145 NaCl). After the treatment with *staphylococci* the polymer surface was rinsed with a physiological saline solution for eliminating loosely attached bacteria. At a subsequent analysis it was determined that no active binding of the *staphylococci* had taken place. The analysis was carried out by determining bacterial cell mass ATP (adenosine triphosphate) out by means of bio luminiscons technique. In short the analysis is carried out by incubating the polymer surface with 50 μl of 1.25 N trichloro acetic acid to extract cellular ATP. The amount of ATP is determined and compared with a standard curve for ATP in a Luminometer 1250 a trade name for a meter for measuring bioluminescence by LKB-Produktor of Bromma, Sweden.

We claim:

1. A vaccine composition comprising an isolated fibronectin binding protein derived from *Staphylococcus aureus* in an amount effective to provide protection from disease caused by *Staphylococcus aureus* infection in a bovine or human and a pharmaceutically acceptable vaccine carrier therefor, wherein said fibronectin binding protein is a *S. aureus* fibronectin binding protein with a molecular weight of 165,000 daltons, or a mixture of a *S. aureus* fibronectin binding protein with a molecular weight of 87,000 daltons and a *S. aureus* fibronectin binding protein with a molecular weight of 165,000 daltons.

2. The vaccine composition as claimed in claim 1 wherein the level of protein is sufficient to provide protection upon challenge with a *Staphylococcus aureus* bacterial strain in a bovine.

3. The vaccine composition as claimed in claim 1 wherein the level of protein is sufficient to provide protection upon challenge with a *Staphylococcus aureus* bacterial strain in a human.

4. A vaccine composition comprising an effective amount of an isolated protein derived from *Staphylococcus aureus*, said protein having the ability to bind fibronectin and a molecular weight of 165,000 daltons, said effective amount of said protein being sufficient to provide protection from disease caused by *Staphylococcus aureus* infection in a bovine or human upon challenge with a *Staphylococcus aureus* bacterial strain, and a pharmaceutically acceptable vaccine carrier therefor.

5. The vaccine composition as claimed in claim 4 wherein the level of protein is sufficient to provide protection upon challenge with a *Staphylococcus aureus* bacterial strain in a bovine.

6. The vaccine composition as claimed in claim 4 wherein the level of protein is sufficient to provide protection upon challenge with a *Staphylococcus aureus* bacterial strain in a human.

7. A vaccine composition for the treatment of mastitis in a bovine or human, said vaccine comprising an effective amount of an isolated fibronectin binding protein derived from *Staphylococcus aureus*, wherein said effective amount of said protein provides protection from disease caused by *Staphylococcus aureus* infection in said bovine or said human and a pharmaceutically acceptable vaccine carrier therefor, wherein said fibronectin binding protein is a *S. aureus* fibronectin binding protein with a molecular weight of 165,000 daltons, or a mixture of a *S. aureus* fibronectin binding protein with a molecular weight of 87,000 daltons and a *S. aureus* fibronectin binding protein with a molecular weight of 165,000 daltons.

8. A method for preventing or treating mastitis in a bovine or human, said method comprising vaccinating said bovine or said human in need of such prevention or treatment with an effective amount of an isolated fibronectin binding protein derived from *Staphylococcus aureus*, wherein said effective amount provides protection from disease caused by *Staphylococcus aureus* infection in said bovine or said human, wherein said fibronectin binding protein is a *S. aureus* fibronectin binding protein with a molecular weight of 165,000 daltons, or a mixture of a *S. aureus* fibronectin binding protein with a molecular weight of 87,000 daltons and a *S. aureus* fibronectin binding protein with a molecular weight of 165,000 daltons.

* * * * *